United States Patent
Sloan

(10) Patent No.: US 8,211,064 B2
(45) Date of Patent: Jul. 3, 2012

(54) CATHETER SECUREMENT DEVICE

(75) Inventor: Gregory A. Sloan, Ann Arbor, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 678 days.

(21) Appl. No.: 12/008,627

(22) Filed: Jan. 11, 2008

(65) Prior Publication Data

US 2009/0182283 A1 Jul. 16, 2009

(51) Int. Cl.
*A61M 5/32* (2006.01)

(52) U.S. Cl. ........................................................ 604/179

(58) Field of Classification Search .................. 604/174, 604/179, 180
See application file for complete search history.

(56) References Cited

U.S. PATENT DOCUMENTS

| | | | | |
|---|---|---|---|---|
| 6,283,945 | B1 * | 9/2001 | Bierman | 604/174 |
| 2005/0182368 | A1 * | 8/2005 | Gillis et al. | 604/180 |
| 2007/0142784 | A1 * | 6/2007 | Dikeman et al. | 604/174 |

* cited by examiner

*Primary Examiner* — Kevin C Sirmons
*Assistant Examiner* — Bradley Osinski
(74) *Attorney, Agent, or Firm* — Bill C. Panagos; Linda D. Kennedy; Rader, Fishman & Grauer PLLC

(57) ABSTRACT

A catheter securement device includes a planar base having an adhesive side for attaching the base to a patient and a mounting side. A receptacle adapted to nest a catheter hub therein is mounted on the mounting side of the base. The receptacle is generally U-shaped in cross-section and is open along a top surface to receive a catheter hub. The receptacle has opposite side walls and front and rear ends. An endless elastic member is retained by one side wall of the receptacle. The endless elastic member is capable of manipulation and stretching over the opening in the top surface and beyond the opposite side wall of the receptacle to retain a catheter hub nested in the receptacle. A flange extends outwardly at the top surface of the opposite side wall to keep the elastic member in place when nesting a catheter hub in the receptacle.

7 Claims, 4 Drawing Sheets

CATHETER SECUREMENT DEVICE

TECHNICAL FIELD

This invention relates to catheter securement devices, and more particularly to catheter securement devices for securing catheters to a patient's body.

BACKGROUND OF THE INVENTION

In the medical field, it is known that patient medical devices such as catheters (and their associated hubs), medical connectors, IV extension sets, medical tubing, and the like, must be secured to a patient to limit or prevent disturbance, movement, or dislodgement of the medical devices. For example, once a catheter is introduced into a patient's vein, it is necessary to stabilize and secure the catheter to prevent movement or dislodgement of the catheter. Any movement of the catheter could work the catheter loose or create an in-and-out or up-and-down catheter tip movement, which can cause blood vessel wall irritation or damage. As a result, an unstabilized catheter is generally a source of discomfort and potential infection for a patient.

Further, the hard edges of patient medical devices, when pressed and secured directly against a patient's bare skin, can be a source of discomfort to the patient. This is especially true when patient medical devices are kept secured to a patient for days or longer.

Conventionally, patient medical devices such as catheters and the like are secured by taping the catheter hub and associated connectors, tubing, and/or extension sets directly against the patient's skin. This method, however, has numerous deficiencies, including insufficient securement and stabilization of the patient medical devices as well as patient discomfort.

SUMMARY OF THE INVENTION

The present invention provides a catheter securement device that securely retains a catheter hub and mounts on a patient's skin. The catheter securement device anchors a catheter hub to a patient and acts to prevent dislodgement of the catheter from the patient. The catheter securement device also provides a cushion between the catheter hub and a patient's skin, thereby improving patient comfort while the catheter remains inserted in the patient.

More particularly, a catheter securement device in accordance with the invention includes a planar base having an adhesive side for attaching the base to a patient and a mounting side. A receptacle adapted to nest a catheter hub therein is mounted on the mounting side of the base. The receptacle is generally U-shaped in cross-section and is open along a top surface to receive a catheter hub. The receptacle has opposite side walls and front and rear ends. An endless elastic member is retained by one side wall of the receptacle. The endless elastic member is capable of manipulation and being stretched over the opening in the top surface and beyond the opposite side wall of the receptacle to retain a catheter hub nested in the receptacle. A flange extends outwardly at the top surface of the opposite side wall to keep the endless elastic member in place when nesting a catheter hub in the receptacle.

In one embodiment, the catheter securement device may include flanges extending outwardly from the front and rear ends of the receptacle at the top surface. The flanges further keep the elastic member in place when nesting a catheter hub in the receptacle. The opening in the receptacle may have a shape that corresponds with a shape of a catheter hub. The endless elastic member may include a tab.

The catheter securement device also may include a release liner releasably mounted on the adhesive side of the base. The release liner may include a first member and a second member. Each of the first member and second member includes a first portion mounted on the adhesive side of the base and a second portion folded relative to the first portion to form a gripping tab. Each gripping tab extend beyond an outer edge of the base. One of the first and second members can be released from the adhesive side of the base without tampering with the other of the members.

The base of the catheter securement device may be made of a polymeric material or similar. The elastic member may be made of a silicone material or similar. The receptacle may be injection molded or similar.

These and other features and advantages of the invention will be more fully understood from the following detailed description of the invention taken together with the accompanying drawings.

DETAILED DESCRIPTION OF THE INVENTION

Figure 1:
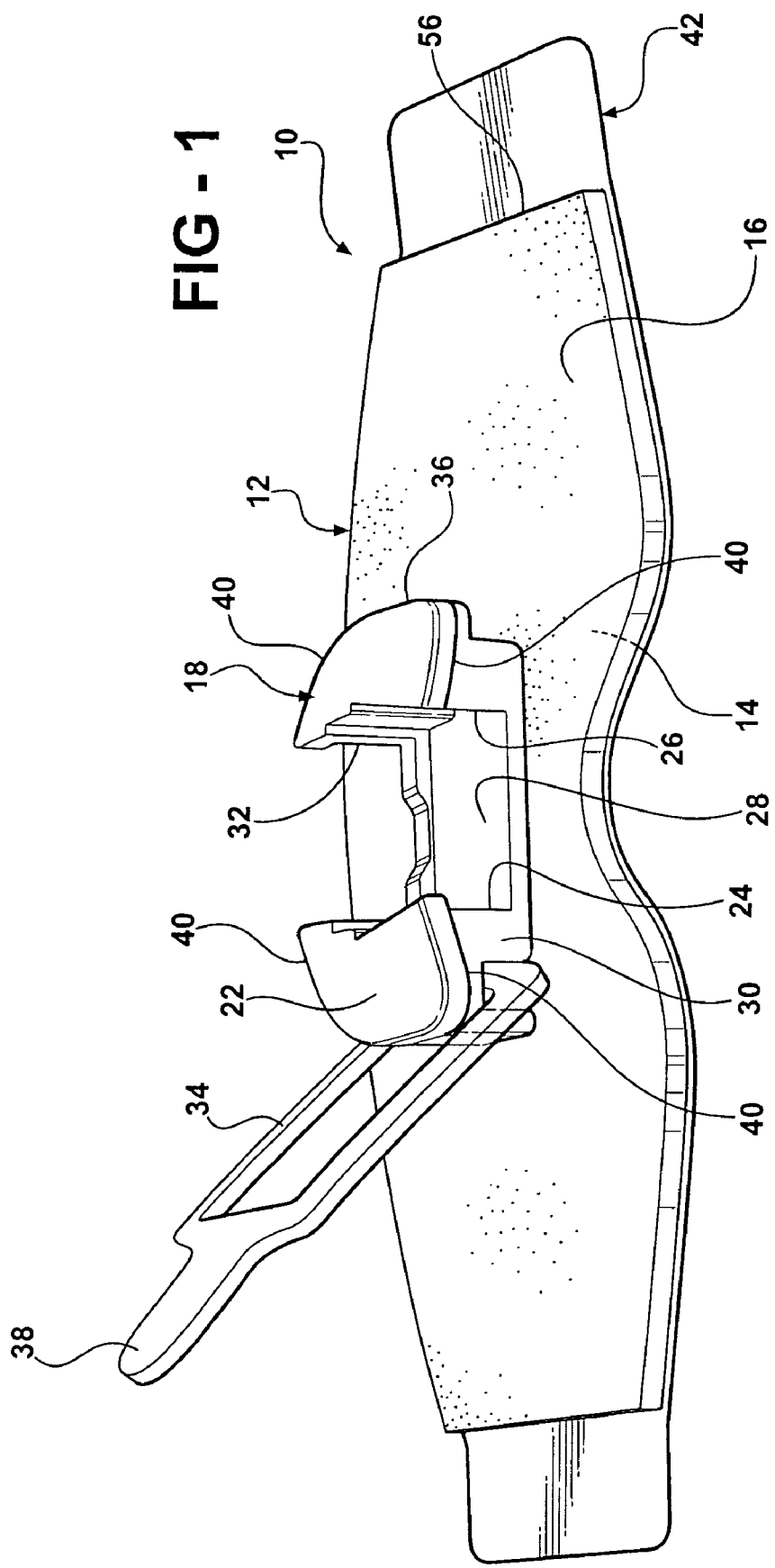
FIG. 1 is a perspective view of a catheter securement device in accordance with the invention.

Referring now to the drawings in detail, numeral 10 generally indicates a catheter securement device in accordance with the invention. The catheter securement device 10 provides for the secure anchoring of a catheter hub to a patient's skin.

With reference to FIGS. 1 through 4, the catheter securement device 10 includes a planar base 12 having an adhesive side 14 for attaching the base to a patient and a mounting side 16. The base 12 may be made of a polymeric material or similar such as a woven material, a non-woven material, a foam material, a mesh material, a net material, a tricot material, an extruded cast material, a punch perforated material, a die cut material, and the like. The base 12 is shown as a single layer of material, although it is within the scope of the invention for the base to be formed of multiple layers of material. The adhesive on the adhesive side 14 of the base 12 may be a medical skin contact grade adhesive that is suitable for adherence to a patient's skin.

A receptacle 18 adapted to nest a catheter hub 20 therein is mounted on the mounting side 16 of the base 12. The receptacle may be mounted to the base by gluing, solvent bonding, ultrasonic welding, RF or other heat sealing, UV curable gluing, or other similar mounting method. The receptacle 18 is generally U-shaped in cross-section and is open along a top surface 22 to receive the catheter hub 20. The receptacle 18 includes opposite side walls 24, 26 and a floor 28 that together define the opening in the receptacle. The opening in the receptacle 18 has a shape that corresponds with a shape of the catheter hub 20. The receptacle 18 also has a front end 30 and a rear end 32.

An endless elastic member 34 is retained by one side wall 24 of the receptacle 18. The endless elastic member 34 may be adjacent the base 12. The endless elastic member 34 may be made of an elastomeric material such as a silicone material or similar. The endless elastic member 34 is capable of manipulation and stretching over the opening in the top surface 22 of the receptacle 18 and beyond the opposite side wall 26 of the receptacle 18 to retain the catheter hub 20 nested in the receptacle. A flange 36 extends outwardly at the top surface 22 of the opposite side wall 26 to keep the endless elastic member 34 in place when nesting the catheter hub 20 in the receptacle 18. The endless elastic member 34 may include a tab 38.

Flanges 40 also extend outwardly from the front and rear ends 30, 32 of the receptacle 18 at the top surface 22. An edge of the flanges 40 may be disposed adjacent the sides 24, 26 of the receptacle 18. The flanges 40 further keep the endless elastic member 34 in place when nesting the catheter hub 20 in the receptacle.

Figure 5:
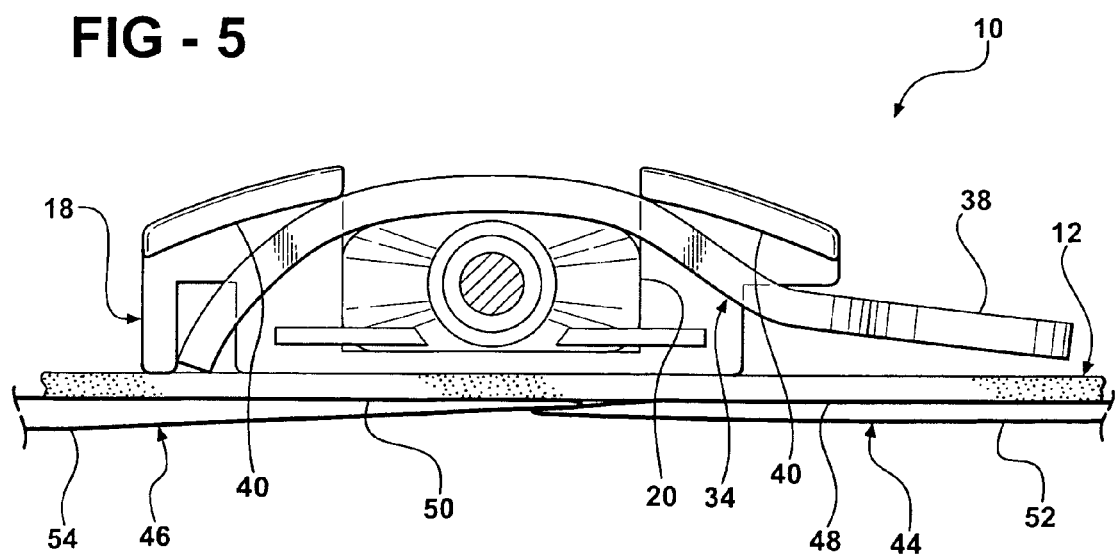
FIG. 5 is a side elevational view of the catheter hub secured in the securement device.

The catheter securement device 10 also may include a release liner 42 releasably mounted on the adhesive side 14 of the base 12. For example, as shown in FIG. 5, the release liner 42 may include a first member 44 and a second member 46. The first member 44 and the second member 46 each includes a first portion 48, 50 mounted on the adhesive side 14 of the base 12 and a second portion 52, 54 folded relative to the first portion to form a gripping tab. The gripping tabs extend beyond an outer edge 56 of the base 12. One of the first and second members 44, 46 can be released from the adhesive side 14 of the base 12 without tampering with the other of the members.

Figure 2:
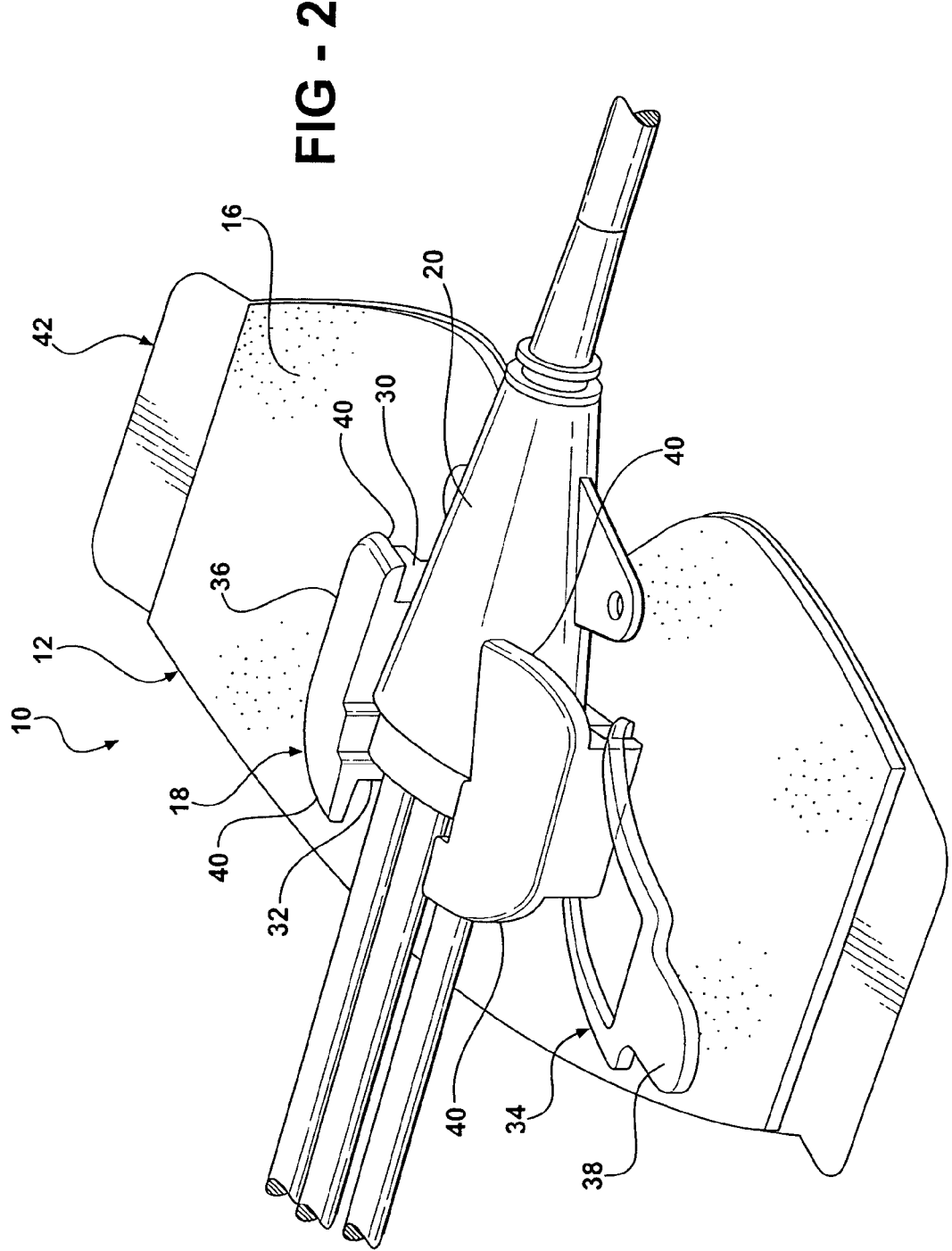
FIG. 2 is a perspective view of a catheter hub inserted into the catheter securement device wherein an endless elastic member of the catheter securement device is in an open position.

A catheter hub 20 can be inserted into the opening in the receptacle 18 when the endless elastic member 34 is in an open position as shown in FIG. 2. When inserted, the outer edges of the catheter hub 20 are in close tolerance (i.e., snugly fit) within the side walls 24, 26 of the receptacle 18, thereby limiting lateral movement of the catheter hub in the receptacle. To secure the catheter hub 20 in the receptacle, the endless elastic member 34 is moved from the open position to a closed position by slightly stretching the endless elastic member over the opening and positioning the endless elastic member underneath the side flange 36 and front and rear flanges 40.

Figure 3:
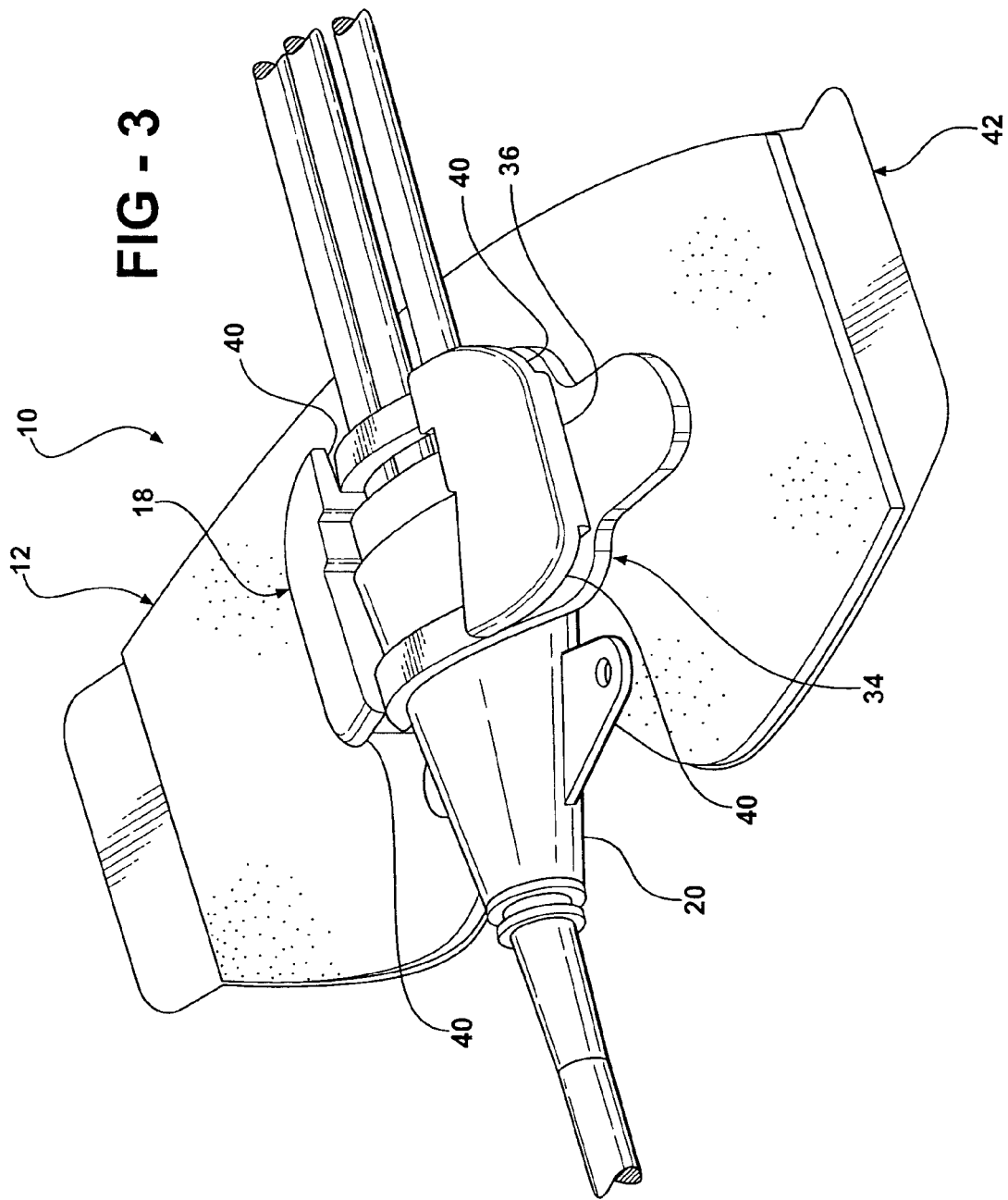
FIG. 3 is a perspective view of a catheter hub inserted into the catheter securement device wherein the endless elastic member is in a closed position to secure the catheter hub in the securement device.
Figure 4:
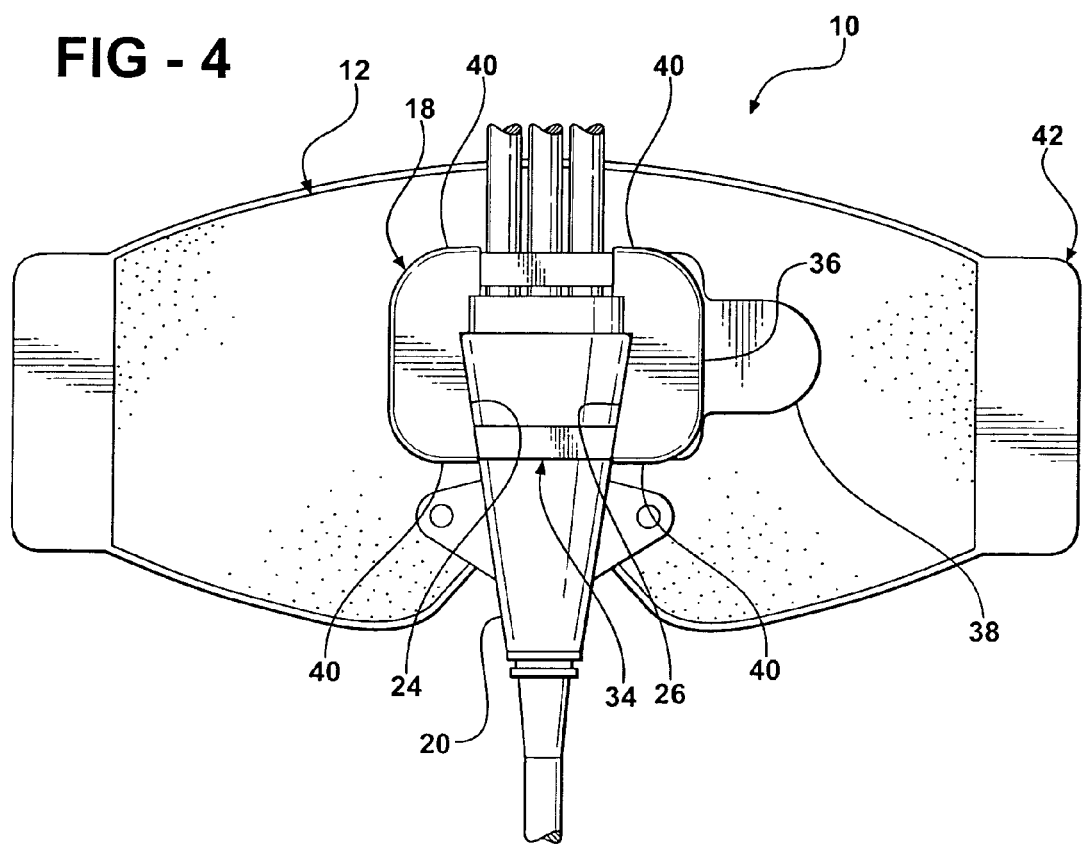
FIG. 4 is a plan view of the catheter hub secured in the securement device.

As shown in FIGS. 3 and 4, in the closed position the flanges 36, 40 are disposed close to the catheter hub 20 and prevent the endless elastic member 34 from moving upward. In turn, the endless elastic member 34 and flanges 36, 40 prevent the catheter hub 20 from moving out of the opening in the receptacle 18. It is apparent that although the endless elastic member 34 is made of an elastomeric material, the endless elastic member prevents the catheter hub 20 from moving because it is relatively thick and incompressible. Further, as shown in FIG. 5, a vertical gap exists between the top of the catheter hub 20 and the bottom side of the flanges 40. The vertical gap is just large enough to receive the endless elastic member 34 between the catheter hub 20 and flanges 40, allowing the endless elastic member to be moved between the open and closed positions. In contrast, no gap exists between the sides of the catheter hub 20 and the inside edges of the flanges 40. Therefore, when the endless elastic member 34 is in the closed position, there is no space for the endless elastic member 34 to fit into if the catheter hub 20 is pulled in a vertical direction. This configuration securely forces the catheter hub 20 to remain nested in the receptacle 18 when the endless elastic member 34 is in the closed position.

Once the catheter hub 20 is secured in the catheter securement device 10, the release liner 42 can be removed from the adhesive side 14 of the base 12. The base 12 can then be placed on an appropriate location of a patient's body to adhere the catheter securement device 10 to the patient. Alternatively, the catheter securement device 10 may be adhered to a patient's skin prior to securing the catheter hub 20 in the receptacle 18 in the manner described above.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A catheter securement system comprising:
   a planar base having an adhesive side for attaching the base to a patient and a mounting side;
   a receptacle mounted on the mounting side of the base;
   said receptacle having a generally U-shaped cross-section with a catheter hub shaped cooperatively with the receptacle, the catheter hub being in said receptacle, the receptacle being open along a top surface;
   said receptacle having front and rear ends and opposite elongated vertical side walls, the vertical side walls further having a length longitudinally extending between said front and rear ends;
   an endless elastic member retained by one elongated side wall of the receptacle;
   said endless elastic member capable of manipulation and being stretched over the opening in the top surface and beyond the opposite elongated side wall of the receptacle to retain the catheter hub; and
   a flange extending outwardly at the top surface of the opposite elongated vertical side wall, the flange extending beyond the length of the opposite elongated side wall at front and rear ends, to keep said endless elastic member in place.

2. The catheter securement system of claim 1, wherein said endless elastic member includes a tab.

3. The catheter securement system of claim 1, including a release liner releasably mounted on said adhesive side of said base.

4. The catheter securement system of claim 1, wherein said release liner includes a first member and a second member, each of the first member and second member including a first portion mounted on said adhesive side of said base and a second portion folded relative to said first portion to form a gripping tab;
   said gripping tabs extending beyond an outer edge of said base;
   whereby one of said first and second members can be released from said adhesive side of said base without tampering with the other of said members.

5. The catheter securement system of claim 1, wherein said base is made of a polymeric material.

6. The catheter securement system of claim 1, wherein said elastic member is made of a silicone material.

7. The catheter securement system of claim 1, wherein said receptacle is injection molded.

* * * * *